United States Patent
Koka

(10) Patent No.: US 12,311,172 B2
(45) Date of Patent: *May 27, 2025

(54) SYSTEMS AND METHODS FOR MEASURING EVOKED RESPONSES FROM A BRAIN OF A PATIENT

(71) Applicant: Advanced Bionics AG, Staefa (CH)

(72) Inventor: Kanthaiah Koka, Valencia, CA (US)

(73) Assignee: Advanced Bionics AG, Staefa (CH)

(*) Notice: Subject to any disclaimer, the term of this patent is extended or adjusted under 35 U.S.C. 154(b) by 0 days.

This patent is subject to a terminal disclaimer.

(21) Appl. No.: 18/439,039

(22) Filed: Feb. 12, 2024

(65) Prior Publication Data
US 2024/0181254 A1   Jun. 6, 2024

Related U.S. Application Data

(63) Continuation of application No. 17/524,342, filed on Nov. 11, 2021, now Pat. No. 11,931,576, which is a
(Continued)

(51) Int. Cl.
*A61N 1/36* (2006.01)
*A61B 5/00* (2006.01)
(Continued)

(52) U.S. Cl.
CPC .......... *A61N 1/36039* (2017.08); *A61B 5/125* (2013.01); *A61B 5/38* (2021.01);
(Continued)

(58) Field of Classification Search
CPC . A61B 5/04001; A61B 5/04845; A61B 5/125; A61B 5/4836; A61B 5/6803;
(Continued)

(56) References Cited

U.S. PATENT DOCUMENTS 8,086,319 B2   12/2011   van Dijk
8,170,678 B2    5/2012   Polak
(Continued)

FOREIGN PATENT DOCUMENTS

WO   2010025504 A1   3/2010
WO   2013116161      8/2013
(Continued)

OTHER PUBLICATIONS

Hay-McCutcheon, Marcia, et al., "Comparison of electrically evoked whole-nerve action potential and electrically evoked auditory brainstem response thresholds in nucleus CI24R cochlear implant recipients", J Am Acad Audiol 13: 416-427 (2002), Department of Speech Pathology and Audiology and Department of Otolaryngology—Head and Neck Surgery, University of Iowa, Iowa City, Iowa.
(Continued)

*Primary Examiner* — Scott Luan
(74) *Attorney, Agent, or Firm* — ALG Intellectual Property, LLC

(57) ABSTRACT

An illustrative system includes a sound processor configured to be worn by a patient and to direct a cochlear implant implanted within the patient to apply electrical stimulation to the patient; and a conductive contact configured to detect a signal representative of an evoked response generated by a brain of the patient, the conductive contact integrated with the sound processor so as to be located between the sound processor and an external surface of a head of the patient while the sound processor is worn by the patient.

20 Claims, 11 Drawing Sheets

Related U.S. Application Data continuation of application No. 16/080,378, filed as application No. PCT/US2016/020141 on Feb. 29, 2016, now Pat. No. 11,185,694.

(51) Int. Cl.
| | | |
|---|---|---|
| *A61B 5/12* | (2006.01) | |
| *A61B 5/38* | (2021.01) | |
| *A61N 1/02* | (2006.01) | |
| *A61N 1/372* | (2006.01) | |
| *H04R 25/00* | (2006.01) | |

(52) U.S. Cl.
CPC .......... *A61B 5/4836* (2013.01); *A61B 5/6803* (2013.01); *A61N 1/025* (2013.01); *A61N 1/36139* (2013.01); *A61N 1/37252* (2013.01); *H04R 25/505* (2013.01); *H04R 25/554* (2013.01); *H04R 25/70* (2013.01); *H04R 2225/021* (2013.01); *H04R 2225/67* (2013.01)

(58) Field of Classification Search
CPC .. A61B 5/24; A61B 5/38; A61N 1/025; A61N 1/0541; A61N 1/36036; A61N 1/36039; A61N 1/36139; A61N 1/37252; H04R 2225/021; H04R 2225/67; H04R 25/505; H04R 25/554; H04R 25/70
See application file for complete search history.

(56) References Cited

U.S. PATENT DOCUMENTS

| | | |
|---|---|---|
| 8,364,274 B1 | 1/2013 | Litvak |
| 9,008,340 B2 | 4/2015 | Ku et al. |
| 9,025,800 B2 | 5/2015 | Kidmose et al. |
| 2008/0249589 A1 | 10/2008 | Cornejo Cruz et al. |
| 2009/0259277 A1 | 10/2009 | Cornejo Cruz et al. |
| 2012/0029377 A1 | 2/2012 | Polak |
| 2012/0238856 A1 | 9/2012 | Kidmose et al. |
| 2012/0245655 A1 | 9/2012 | Spitzer et al. |
| 2013/0006328 A1 | 1/2013 | Bouchataoui et al. |
| 2014/0038147 A1 | 2/2014 | Morrow |
| 2015/0018699 A1 | 1/2015 | Zeng |
| 2016/0157030 A1 | 6/2016 | Odame |

FOREIGN PATENT DOCUMENTS

| | | |
|---|---|---|
| WO | 2013142843 | 9/2013 |
| WO | 2015130318 | 9/2015 |

OTHER PUBLICATIONS

International Search Report and Written Opinion received in International Application No. PCT/US16/020141, dated Oct. 25, 2016.

Kirby, Benjamin, et al., "Relationships between Electrically Evoked Potentials and Loudness Growth in Bilateral Cochlear Implant Users, Ear Hear", May 2012, 33(3): 389-398. NIH Public Access Author Manuscript.

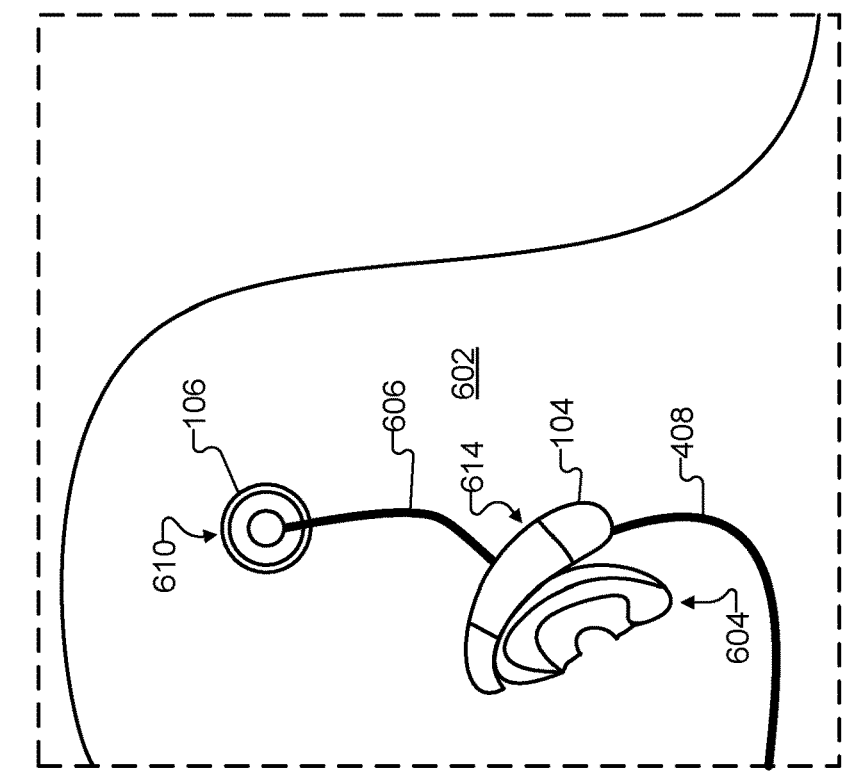
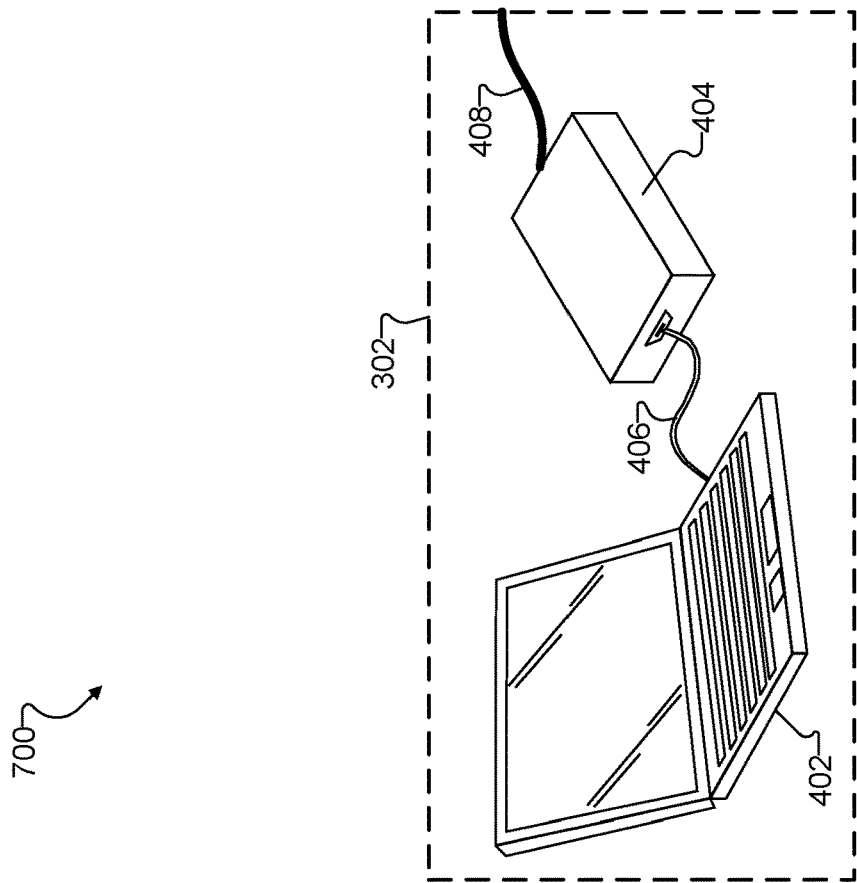
Fig. 7

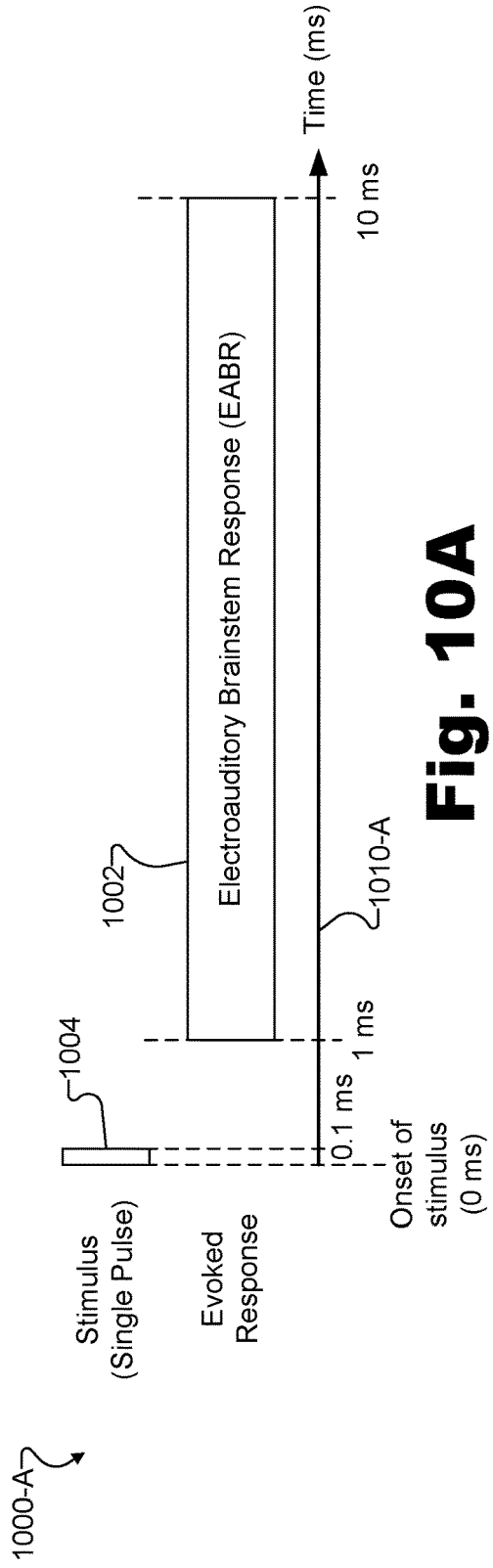
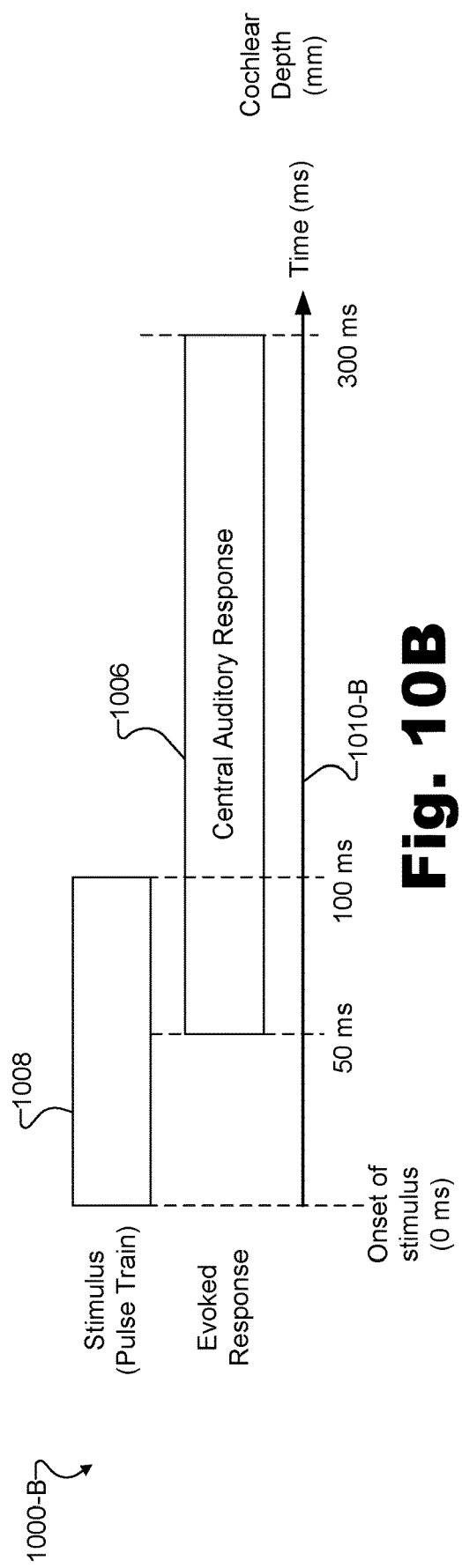

SYSTEMS AND METHODS FOR MEASURING EVOKED RESPONSES FROM A BRAIN OF A PATIENT

RELATED APPLICATIONS

The present application is a continuation of U.S. patent application Ser. No. 17/524,342 filed Nov. 11, 2021, which is a continuation of U.S. patent application Ser. No. 16/080,378 filed Aug. 28, 2018, and issued as U.S. Pat. No. 11,185,694, which is a U.S. National Stage Application under 35 U.S.C. § 371 of International Application No. PCT/US2016/020141 filed Feb. 29, 2016. Each of these applications are hereby incorporated by reference in their entireties.

BACKGROUND INFORMATION

In various medical contexts, it is often desirable to provide stimulation (e.g., audible stimulation, electrical stimulation, etc.) to a patient and to measure an evoked response to the stimulation generated by the patient's brain. For example, various techniques for evoking and recording auditory brainstem responses ("ABRs") using audible stimulation are commonly used for newborn hearing screening, determining the type and/or degree of hearing loss in mature patients, detecting lesions in the auditory nerve or brainstem, and for various other applications.

In certain examples, it may also be desirable to elicit and measure evoked responses in cochlear implant patients or prospective cochlear implant patients. However, measuring evoked responses in cochlear implant patients may require overcoming certain challenges. For example, because these patients may have little or no ability to hear audible stimulation, modifications to typical ABR techniques may include replacing audible stimulation (e.g., an audible click) with electrical stimulation (e.g., an electrical pulse applied to the patient via a cochlear implant system). Certain evoked responses measured based on such electrical stimulation may be referred to as electroauditory brainstem responses ("EABRs"), and may be used to facilitate "fitting" a cochlear implant system to a patient (e.g., calibrating the cochlear implant system to generate stimulation at levels tailored to the patient's characteristics and/or comfort preferences) or assessing the cochlear implants effectiveness on the patient. In particular, it may be useful to measure EABRs of patients (e.g., small children, patients with severe disabilities, and/or unconscious patients) who are unable to provide verbal feedback about their preferences. Additionally, it may be desirable to measure other types of evoked responses in a cochlear implant patient. For example, central auditory responses (e.g., cortical auditory evoked potentials ("CAEPs"), auditory steady state responses ("ASSRs"), etc.) may be measured to assess how the patient is responding to the cochlear implant system, whether fitting adjustments should be made, etc.

Conventionally, measuring evoked responses (e.g., ABRs, EABRs, etc.) from a patient involves attaching a plurality of electrodes to the patient's head and using a specialized measurement machined such as an ABR machine to detect, record, and process signals representative of the evoked responses. As such, the ABR machine typically must be synchronous to the source of stimulation so that stimulus artifacts (e.g., undesirable noise on the signal representative of the evoked response that is caused by the stimulation itself, rather than the patient's brain) may properly be identified and removed. For cochlear implant patients, this means that the ABR machine must coordinate with the cochlear implant system using trigger signals or other similar means that require additional setup (e.g., additional cable connections, etc.) and/or create additional issues (e.g., radio frequency ("RF") artifacts on the signal representative of the evoked response, etc.). Additionally, an ABR machine may be inconvenient or non-ideal in the cochlear implant system context for various other reasons such as a relatively large size or expensive cost of the ABR machine, a limitation of the ABR machine's capabilities to only measure ABR and/or EABR evoked responses rather than central auditory responses and/or other evoked responses having relatively long latencies, and extra equipment (e.g., dedicated electrodes) and equipment setup required for proper operation of the ABR machine.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIGS. 6-9 illustrate exemplary implementations of the evoked response measurement system of FIG. 5 according to principles described herein.

FIGS. 10A and 10B illustrate exemplary timing diagrams of evoked responses to different types of stimulation according to principles described herein.

DETAILED DESCRIPTION

Figure 1:
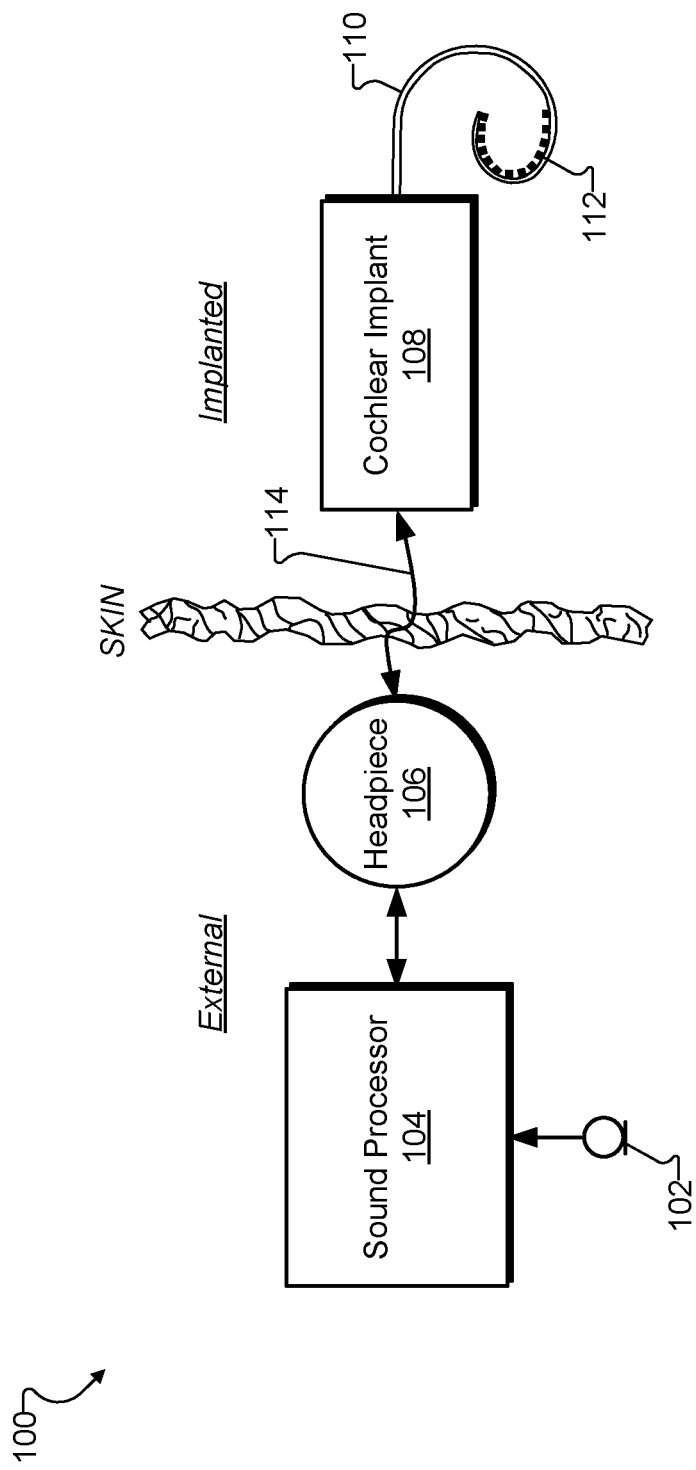
FIG. 1 illustrates an exemplary cochlear implant system according to principles described herein.

Systems and methods for measuring evoked responses from a brain of a patient are described herein. For example, an exemplary evoked response measurement system may include a sound processor external to a patient and configured to direct a cochlear implant implanted within the patient to apply electrical stimulation to the patient. The evoked response measurement system may also include a headpiece separate from the sound processor that may be configured to connect to the sound processor by way of a cable and to affix to an external surface of a head of the patient. The headpiece may be further configured to facilitate wireless communication between the sound processor and the cochlear implant. For example, the headpiece may include a coil configured to transmit a wireless signal from the sound processor to a corresponding coil implanted within the patient and associated with the cochlear implant.

The evoked response measurement system may further include a plurality of conductive contacts communicatively coupled to the sound processor. The plurality of conductive contacts may be configured to be affixed to the external surface of the head of the patient and to detect a signal representative of an evoked response (e.g., an EABR, a central auditory response, etc.) generated by a brain of the patient in response to the electrical stimulation applied by the cochlear implant. In some examples, the plurality of conductive contacts may include a first conductive contact physically coupled to the headpiece and configured to be located between the headpiece and the external surface of the head of the patient while the headpiece is affixed to the external surface of the head of the patient. Additional conductive contacts within the plurality of conductive contacts may be located in other suitable locations. For example, an additional conductive contact may be physically coupled to the sound processor or to an additional headpiece.

As will be described below, the systems and methods described herein may be used to measure evoked responses from a brain of a patient without the use of an additional ABR machine or other measurement/recording machine. As a result, the systems and methods described herein may facilitate measuring evoked responses more accurately and conveniently. For example, because components of the cochlear implant system (e.g., the sound processor) and/or a programming system communicatively coupled with the cochlear implant system perform both 1) directing the cochlear implant to apply electrical stimulation and 2) recording a signal representative of an evoked response elicited by the stimulation, the cochlear implant system may not need to remain synchronized with another device such as an ABR machine in order to accurately remove stimulus artifacts from the signal representing evoked responses. Since the cochlear implant system and/or the programming system directs the electrical stimulation to be generated and applied, the cochlear implant system and/or the programming system are already aware of when the electrical stimulation was applied.

Additionally, it may be significantly more convenient to measure evoked responses using the sound processor, a relatively portable programming system, and/or a plurality of conductive contacts integrated with components of the cochlear implant system that are already attached or in close proximity to the patient's head (e.g., the headpiece and/or the sound processor), rather than by using a relatively large ABR machine receiving input from a plurality of electrodes attached to the patient's head only for the purposes of measuring the evoked responses. Moreover, the disclosed methods and systems may be used to measure certain evoked responses (e.g., central auditory responses) that are generated by the brain after relatively long latencies (e.g., greater than ten milliseconds ("ms")), while conventional ABR machines may not be configured to properly record such evoked responses at all. Eliminating ABR machines and other similar machines from measurements of evoked responses may additionally eliminate costs and other undesirable factors associated with the ABR machines, such as noise caused by the ABR machines that may interfere with the signals being recorded. Other advantages and benefits of the disclosed systems and methods will be discussed and/or made apparent by additional examples and explanation below.

As used herein, an "evoked response" may refer to an EABR, a central auditory response (e.g., a cortical auditory evoked potential (CAEP), an auditory steady state response (ASSR), etc.), or any other evoked potential or evoked response of the brain that is elicited by electrical stimulation presented to the patient. As will be described in more detail below, evoked responses may be measured by detecting (e.g., using a conductive contact) signals representative of the evoked responses (e.g., electrical signals evoked in the brain responsive to stimulation). The signals representative of the evoked responses may be amplified (e.g., to generate amplified versions of the signals), processed (e.g., to generate processed versions of the signals without stimulus artifacts), or otherwise modified as may serve particular implementations.

FIG. 1 illustrates an exemplary cochlear implant system 100. Cochlear implant system 100 may include a microphone 102, a sound processor 104, a headpiece 106 having a coil disposed therein, a cochlear implant 108, and an electrode lead 110 (also referred to as a "lead"). Lead 110 may include an array of electrodes 112 disposed on a distal portion of lead 110 and that are configured to be located within the cochlea after lead 110 is inserted into the cochlea. As shown, lead 110 may be pre-curved so as to fit within the cochlea. Additional or alternative components may be included within cochlear implant system 100 as may serve a particular implementation.

As shown, cochlear implant system 100 may include various components configured to be located external to a patient including, but not limited to, microphone 102, sound processor 104, and headpiece 106. Cochlear implant system 100 may further include various components configured to be implanted within the patient including, but not limited to, cochlear implant 108 and electrode lead 110.

Microphone 102 may be configured to detect audio signals presented to the user. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, input by way of a programming system such as a clinician's programming interface ("CPI") device, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BTE") unit, a body worn device, and/or any other sound processing unit within any housing as may serve a particular implementation. For example, in certain implementations, sound processor 104 may be implemented by an electro-acoustic stimulation ("EAS") sound processor included in an EAS system configured to provide both electrical and acoustic stimulation to a patient.

A sound processor worn behind the patient's here may be referred to herein as a BTE sound processor. As will be described in more detail below, in embodiments where sound processor 104 is a BTE sound processor, sound processor 104 may be physically connected to a conductive contact configured to detect a signal representative of an evoked response generated by the patient's brain.

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108 (e.g., a wireless link between a coil disposed within headpiece 106 and a coil physically coupled to cochlear implant 108). It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bi-directional communication link and/or one or more dedicated uni-directional communication links as may serve a particular implementation). As will be described in more detail below, headpiece 106 may be physically connected to a conductive contact configured to detect a signal representative of an evoked response generated by the patient's brain.

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of cochlear implant that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102, a synthesized audio signal related to fitting (i.e. calibrating) sound processor 104 to comfortable levels for the patient, etc.) in accordance with one or more stimulation parameters transmitted thereto by sound processor 104. Cochlear implant 108 may be further configured to apply the electrical stimulation to one or more stimulation sites (e.g., one or more intracochlear regions) within the patient via one or more electrodes 112 disposed along electrode lead 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

Figure 2:
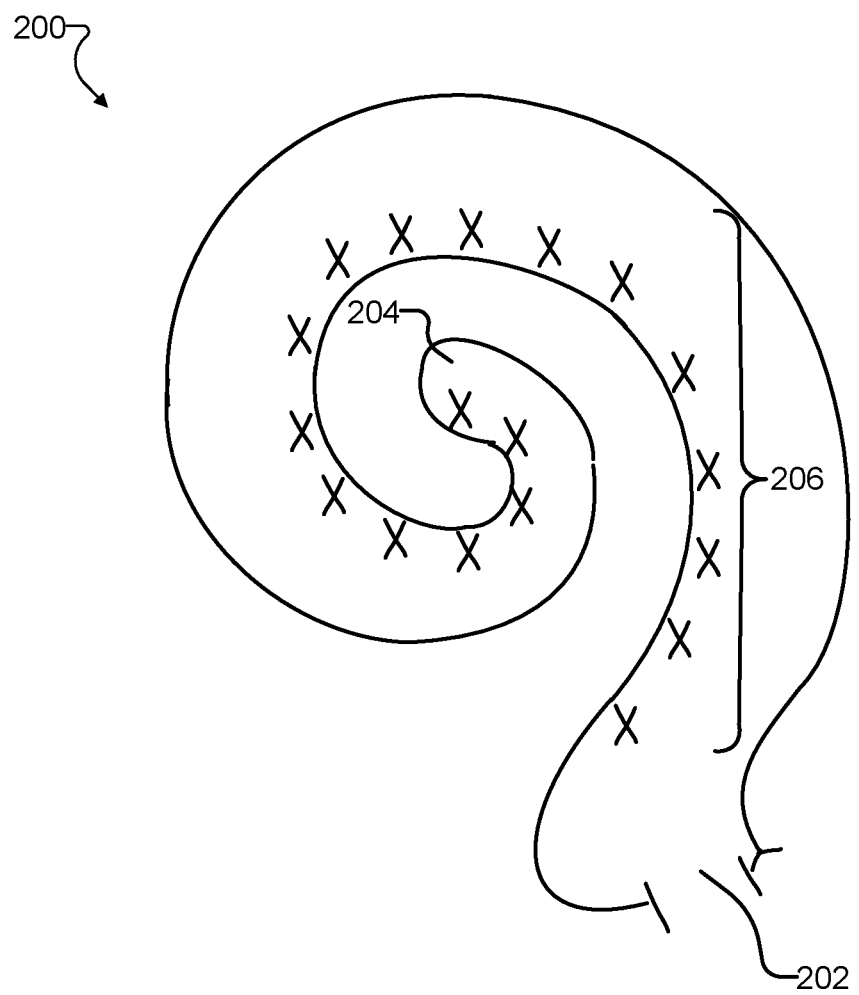
FIG. 2 illustrates a schematic structure of the human cochlea according to principles described herein.

FIG. 2 illustrates a schematic structure of the human cochlea 200 into which electrode lead 110 may be inserted. As shown in FIG. 2, cochlea 200 is in the shape of a spiral beginning at a base 202 and ending at an apex 204. Within cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrodes disposed within the apical region (i.e., "apical electrodes") may result in the patient perceiving relatively low frequencies and electrical stimulation applied by way of electrodes disposed within the basal region (i.e., "basal electrodes") may result in the patient perceiving relatively high frequencies. The delineation between the apical and basal electrodes on a particular electrode lead may vary depending on the insertion depth of the electrode lead, the anatomy of the patient's cochlea, and/or any other factor as may serve a particular implementation.

In some examples, a programming system separate from (i.e., not included within) cochlear implant system 100 may be selectively and communicatively coupled to sound processor 104 in order to perform one or more programming or fitting operations with respect to cochlear implant system 100. For example, the programming system may present audio clips to the patient by way of the cochlear implant system in order to facilitate evaluation of how well the cochlear implant system is performing for the patient.

Figure 3:
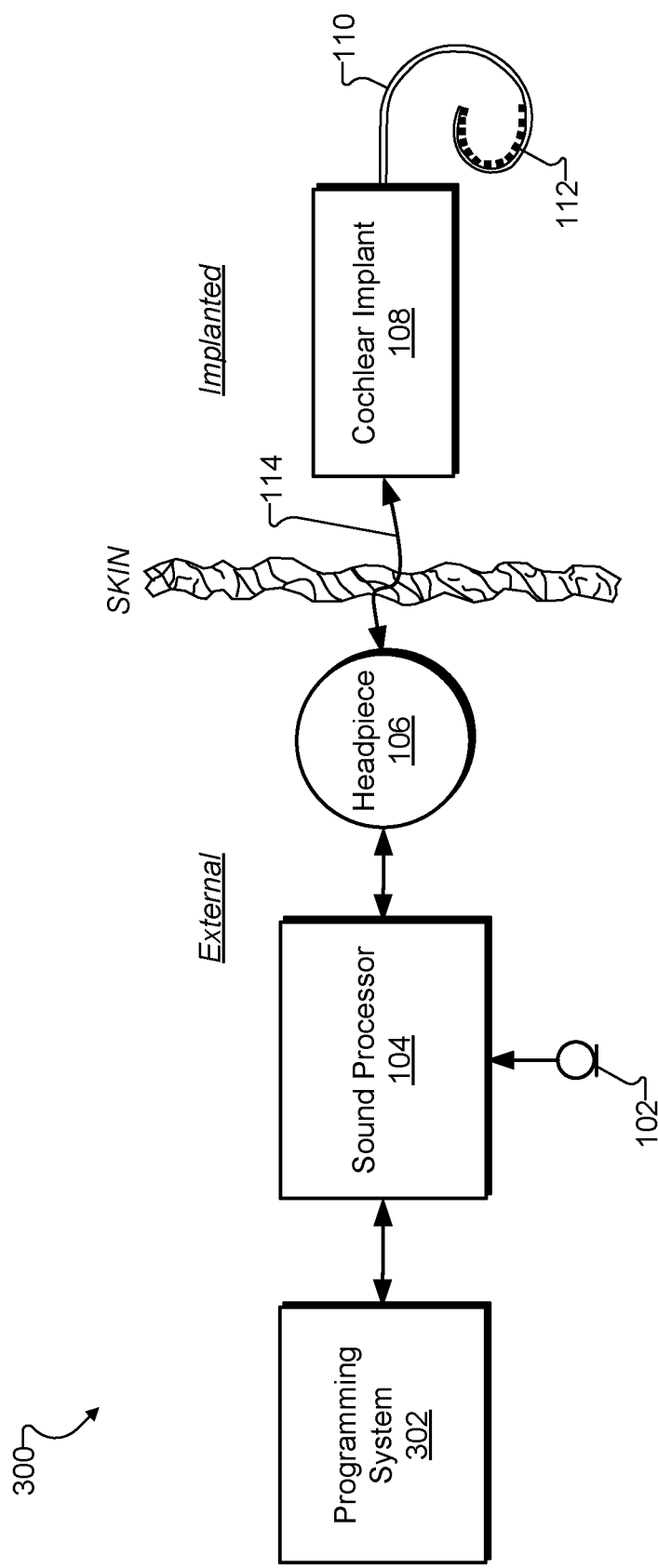
FIG. 3 illustrates an exemplary configuration of the cochlear implant system of FIG. 1 in which a programming system is communicatively coupled to a sound processor according to principles described herein.

To illustrate, FIG. 3 shows an exemplary configuration 300 in which a programming system 302 is communicatively coupled (e.g., by way of a wired or wireless communication channel) to sound processor 104. Programming system 302 may be implemented by any suitable combination of physical computing and communication devices including, but not limited to, a fitting station or device, a programming device, a personal computer, a laptop computer, a handheld device, a mobile device (e.g., a mobile phone), a CPI device, and/or any other suitable component as may serve a particular implementation. In some examples, programming system 302 may provide one or more graphical user interfaces ("GUIs") (e.g., by presenting the one or more GUIs by way of a display screen) with which a clinician or other user may interact.

Programming system 302 may be separate from (i.e., not included within) cochlear implant system 100 and may be selectively and communicatively coupled (e.g., by way of a wired or wireless communication channel) to sound processor 104 in order to perform one or more programming or fitting operations with respect to cochlear implant system 100. For example, programming system 302 may present audio clips to the patient by way of cochlear implant system 100 in order to facilitate evaluation of how well cochlear implant system 100 is performing for the patient. In other examples, as will be described in more detail below, programming system 302 may transmit one or more commands to cochlear implant system 100 (e.g., to sound processor 104) for sound processor 104 to direct cochlear implant 108 to generate particular electrical stimulation (e.g., an electrical pulse, an electrical pulse train, etc.) aimed at evoking from the patient's brain an evoked response such as an EABR or central auditory response.

Figure 4:
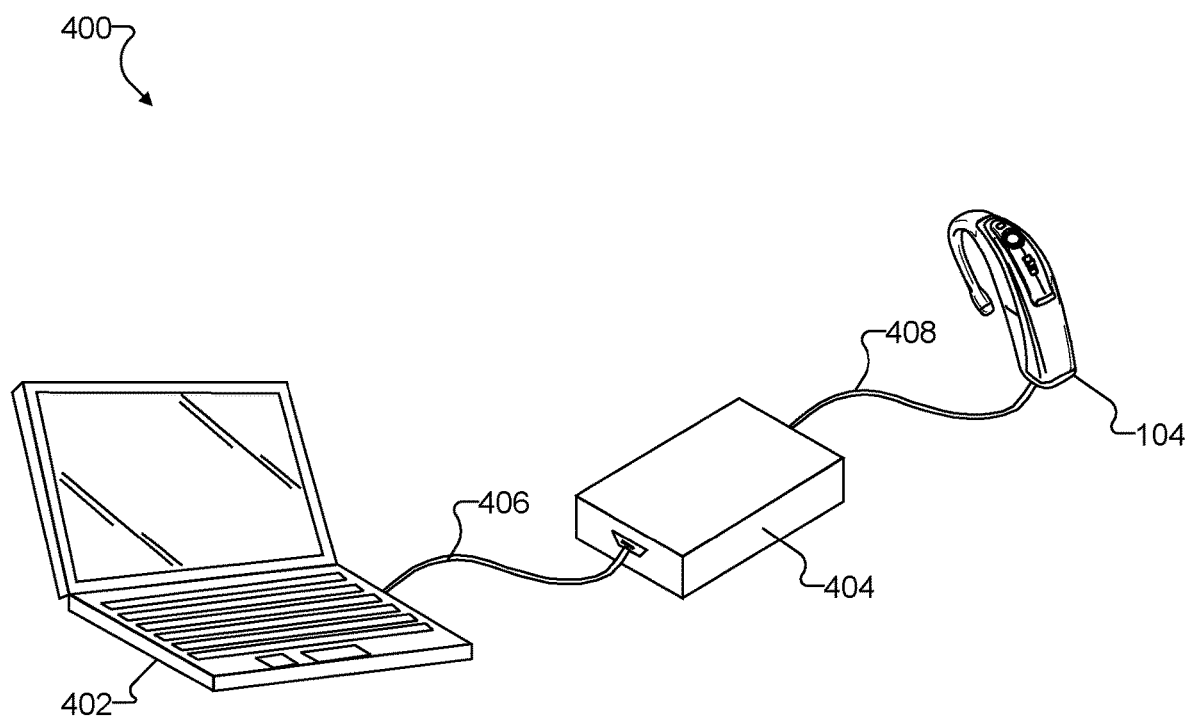
FIG. 4 illustrates an exemplary implementation of a programming system according to principles described herein.

FIG. 4 illustrates an exemplary configuration 400 in which programming system 302 is implemented by a computing device 402 and a CPI device 404. As shown, computing device 402 may be selectively and communicatively coupled to CPI device 404 by way of a cable 406. Likewise, CPI device 404 may be selectively and communicatively coupled to sound processor 104 by way of a cable 408. Cables 406 and 408 may each include any suitable type of cable that facilitates transmission of digital data between computing device 402 and sound processor 104. For example, cable 406 may include a universal serial bus ("USB") cable and cable 408 may include any type of cable configured to connect to a programming port included in sound processor 104.

Figure 5:
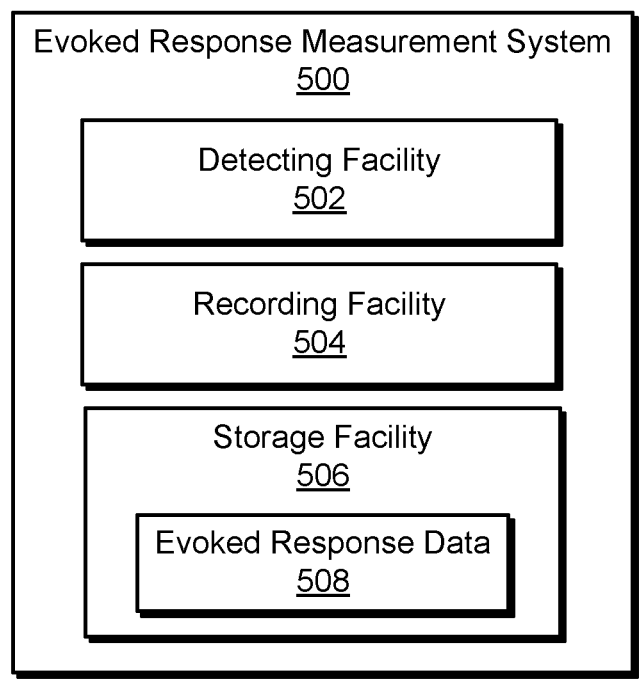
FIG. 5 illustrates exemplary components of an evoked response measurement system according to principles described herein.

FIG. 5 illustrates exemplary components of an evoked response measurement system 500 ("measurement system 500"). Measurement system 500 may be configured to perform any of the operations described herein. As shown, measurement system 500 may include a detecting facility 502, a recording facility 504, and a storage facility 506, which may be in communication with one another using any suitable communication technologies. Storage facility 506 may maintain evoked response data 508 generated, detected, analyzed, recorded, and/or used by detecting facility 502 and/or recording facility 504. Storage facility 506 may maintain additional or alternative data as may serve a particular implementation.

Detecting facility 502 may perform various operations associated with providing stimulation to a patient's brain and detecting a signal representative of an evoked response to the stimulation. For example, detecting facility 502 may be implemented by one or more components of cochlear implant system 100 (described above in relation to FIG. 1 and in relation to configuration 300 of FIG. 3) configured to perform operations aimed at stimulating the patient's brain and detecting the signal representative of the evoked response. Specifically, detecting facility 502 may be implemented by a sound processor external to the patient (e.g., sound processor 104) that may be configured to direct a cochlear implant implanted within the patient (e.g., cochlear implant 108) to apply electrical stimulation to the patient.

For example, the sound processor may be configured to independently run a software program (e.g., a fitting program, an auto-calibration program, etc.) that causes the sound processor to direct the cochlear implant to generate and apply electrical stimulation to the patient's cochlea. The electrical stimulation may include a relatively short pulse (e.g. a 100 microsecond pulse) representative of a "click" sound, a series of short pulses in a pulse train, and/or any other type of electrical stimulation that may serve a particular embodiment. In other examples, the sound processor may direct the cochlear implant to generate and apply the electrical stimulation based on one or more commands received from a programming system implemented by detecting facility 502 (e.g., programming system 302, described above in relation to FIG. 3, or computing device 402 and CPI device 404, described above in relation to FIG. 4).

Detecting facility 502 may also be implemented by a headpiece (e.g., headpiece 106) separate from the sound processor and configured to connect to the sound processor by way of a cable, to affix to an external surface of the head of the patient, and to facilitate wireless communication between the sound processor and the cochlear implant. For example, the headpiece may receive a signal (e.g., a signal representative of a command intended for the cochlear implant) from the sound processor via the cable. The headpiece may use a coil included within the headpiece to transmit the signal wirelessly through the patient's skin to a corresponding coil associated with a cochlear implant implanted within the patient. Similarly, the coil within the headpiece may receive wireless signals transmitted by the coil of the cochlear implant and send them via the cable to the sound processor.

Integrated with the components of cochlear implant system 100 as will be described in more detail below, detecting facility 502 additionally may include a plurality of conductive contacts configured to be affixed to the external surface of the head of the patient and to detect a signal representative of an evoked response generated by the patient's brain in response to the electrical stimulation applied by the cochlear implant of detecting facility 502. The plurality of conductive contacts may be communicatively coupled to the sound processor so as to send the detected signal representative of the evoked response to the sound processor. At least one conductive contact within the plurality of conductive contacts may integrate with the headpiece of detecting facility 502. Specifically, the conductive contact may be physically coupled to the headpiece and configured to be located between the headpiece and the external surface of the head of the patient while the headpiece is affixed to the external surface of the head of the patient. Similarly, as will be described and illustrated below, one or more other conductive contacts within the plurality of conductive contacts may integrate with the sound processor of detecting system 502 or with one or more additional headpieces of detecting facility 502 (e.g., "dummy" headpieces that are configured to affix to the head of the patient but are not necessarily configured to facilitate wireless communication between the sound processor and the cochlear implant). As such, detecting system 502 may provide the electrical stimulation to the patient (e.g., via the cochlear implant, under the direction of the sound processor) and may detect a signal representative of an evoked response to the electrical stimulation (e.g., via the conductive contacts affixed to the head of the patient).

Recording facility 504 may perform various operations associated with receiving, analyzing, filtering, and/or recording signals representative of evoked responses detected by detecting facility 502. To this end, recording facility 504 may similarly be implemented by one or more of the same or different components of cochlear implant system 100 as included within detecting facility 502. Specifically, recording facility 504 may be implemented by the sound processor, which receives the signal representative of the evoked response detected from the patient's brain, and to process the signal by removing (e.g., filtering) at least one stimulus artifact from the signal. Stimulus artifacts removed by recording facility 504 may include any noise introduced to the signal representative of the evoked response that is not indicative of the evoked response itself. For example, certain stimulus artifacts may be representative of (e.g., caused by) the electrical stimulation applied to the patient (e.g., the pulse or the pulse train) rather than the evoked response of the brain to the electrical stimulation. Recording facility 504 may further filter, clean, or analyze the signal representative of the evoked response in any manner that serves a particular implementation.

In certain examples, recording facility 504 may be implemented by a programming system (e.g., programming system 302, described above in relation to FIG. 3, or computing device 402 and CPI device 404, described above in relation to FIG. 4) configured to perform the receiving, analyzing, and/or filtering of the signal representative of the evoked response in addition to or as an alternative to performing these tasks within the sound processor. Additionally, recording facility 504 may be configured to record any signal that may serve a particular implementation. For example, recording facility 504 (e.g., the sound processor and/or the programming system) may record a raw version of the signal representative of the evoked response detected by detecting facility 502, an amplified version of the signal generated by an amplifier within recording facility 504 (e.g., within the sound processor), a processed version of the signal generated by recording facility 504, and/or any other signal or version of the signal that may serve a particular embodiment. For example, recording facility 504 may record and store data representative of a signal in storage facility 506 (e.g., within evoked response data 508) before, during, or after the signal is processed.

Various implementations of measurement system 500 will now be described in relation to FIGS. 6 through 9. It will be recognized that additional implementations of measurement system 500 not explicitly described or illustrated in relation to FIGS. 6 through 9 may also be possible and will be understood to fall within the scope of this disclosure.

Figure 6:
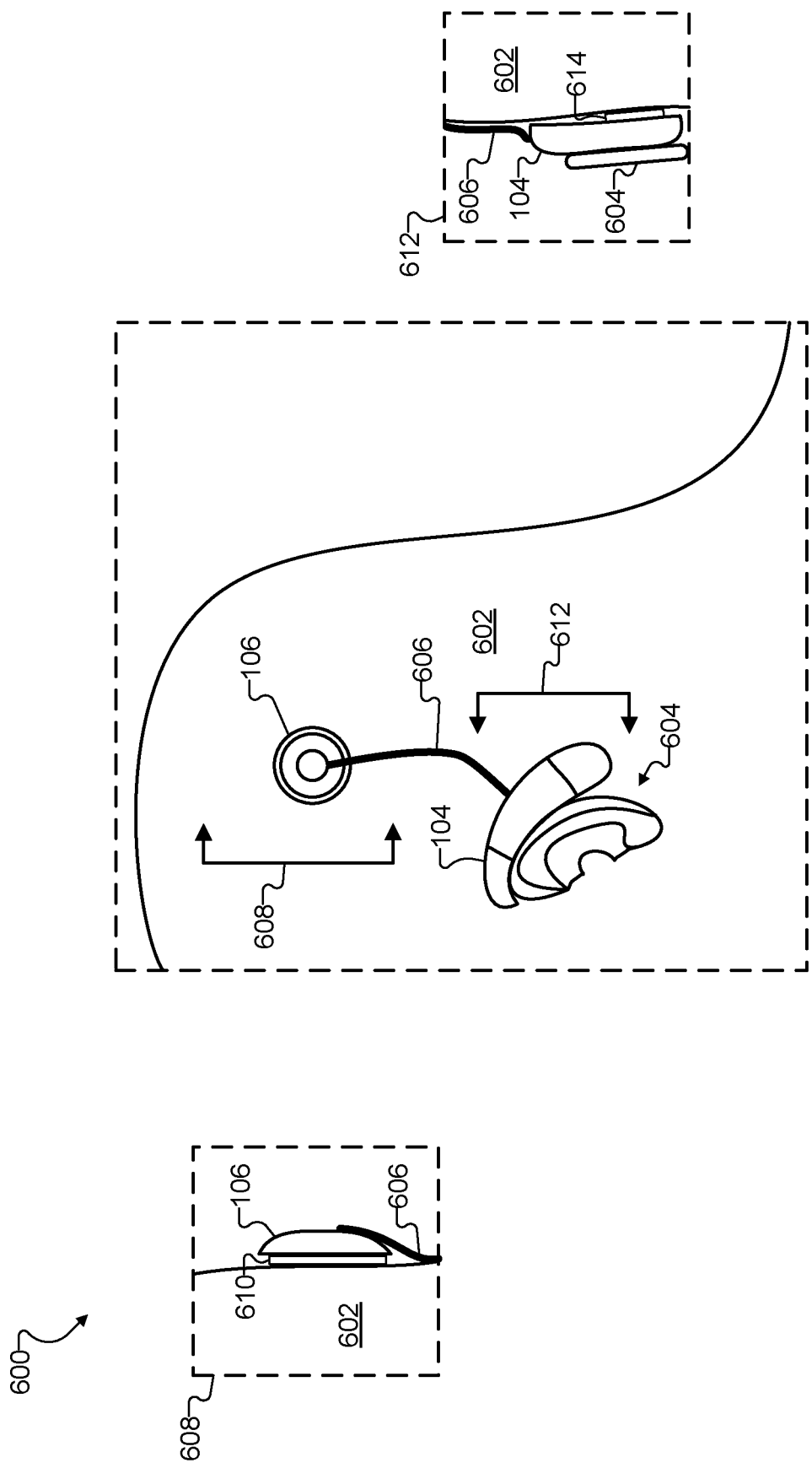

FIG. 6 illustrates a first exemplary implementation 600 of measurement system 500. In operation, as illustrated in FIG. 6, implementation 600 may be attached to, worn by, or otherwise associated with a patient such as by attaching to an external surface 602 of the head of the patient, worn behind an ear 604 of the patient, etc. As shown, implementation 600 may include sound processor 104 communicatively coupled with headpiece 106 by way of a cable 606. Cable 606 may include one or more conductors (e.g., conductive wires) configured to carry electrical signals between sound processor 104 and headpiece 106, such as data signals representative of commands from sound processor 104 to be transmitted by headpiece 106 to a cochlear implant implanted within the patient. Additionally, as will be described in more detail below, cable 606 may include one or more additional conductors configured to carry electrical signals (e.g., signals representative of evoked responses) detected by a conductive contact associated with (e.g., located under) headpiece 106 to sound processor 104.

For example, as illustrated in FIG. 6, a view 608 shows a left-side view of headpiece 106 and cable 606 where a conductive contact 610 is shown to be physically coupled to headpiece 106 (e.g., under headpiece 106) and located between headpiece 106 and external surface 602 of the head of the patient. Conductive contact 610 may be constructed of any suitable conductive material that is configured to detect signals representative of evoked responses from the brain of the patient by being in contact with external surface 602 of the head of the patient. For example, conductive contact 610 may be constructed of a conductive cloth such as a silver cloth, or another conductive material that may serve a particular embodiment.

While no connection is explicitly shown in FIG. 6 between conductive contact 610 and sound processor 104 or cable 606, it will be understood that conductive contact 610 may be communicatively coupled to sound processor 104 in any way that may serve a particular implementation. For example, conductive contact 610 may be communicatively coupled to sound processor 104 by way of a conductive wire separate from cable 606, a conductive wire included within cable 606 (e.g., on the same or a separate conductive wire as a conductive wire carrying signals between sound processor 104 and headpiece 106), a wireless link, or any other suitable connection.

As shown in FIG. 6, sound processor 104 may, in certain examples, be a BTE sound processor configured to be worn by the patient behind ear 604 of the patient. In these examples, the plurality of conductive contacts used to detect the signal representative of the evoked response may include a second conductive contact 614 physically and communicatively coupled to sound processor 104. Specifically, a view 612 shows a right-side view of sound processor 104, ear 604, and cable 606 illustrating that conductive contact 614 may be physically coupled to sound processor 104 (e.g., under sound processor 104) and located between sound processor 104 and external surface 602 of the head of the patient while sound processor 104 is worn by the patient behind ear 604 of the patient.

Like conductive contact 610 shown in view 608, conductive contact 614 may be constructed of any suitable material (e.g., a conductive cloth such as silver cloth) and may be communicatively coupled to sound processor 104 in any suitable way (e.g., by a conductive wire combined with or separate from cable 606, directly wired into sound processor 104, etc.).

As described above in relation to measurement system 500, sound processor 104 may direct a cochlear implant implanted within the head of the patient (e.g., similar to cochlear implant 108 of FIGS. 1 and 3, not shown in FIG. 6) to generate and apply electrical stimulation (e.g., a pulse or a pulse train) to the patient. As further described above, an evoked response may be generated by the brain of the patient in response to the application of the electrical stimulation. To measure the evoked response, sound processor 104 may receive, from conductive contacts 610 and/or 614, a signal representative of the evoked response. Upon receiving the signal representative of the evoked response, sound processor 104 may amplify, analyze, record, or otherwise process the signal as may serve a particular implementation.

For example, sound processor 104 may include an amplifier (e.g., an amplifier located within sound processor 104) for amplifying the signal representative of the evoked response detected by conductive contacts 610 and/or 614. The amplifier may be communicatively coupled with each of conductive contacts 610 and 614 and may be configured to amplify the signal representative of the evoked response to generate an amplified version of the signal representative of the evoked response.

In certain examples, the amplifier may be a shared amplifier configured to operate in a plurality of modes. For example, in a first mode of operation, the shared amplifier may be configured to amplify the signal representative of the evoked response to generate the amplified version of the signal, while in a second mode of operation, the shared amplifier may be configured to amplify an audio signal received by a microphone communicatively coupled with sound processor 104 (e.g., microphone 102, described above in relation to FIG. 1 but not explicitly shown in FIG. 6). The shared amplifier may operate in one or more modes of operation simultaneously or consecutively (i.e., one at a time). For example, the signal representative of the evoked response and the audio signal received by the microphone may be multiplexed or otherwise switched onto an input of the shared amplifier one at a time so that the shared amplifier may switch between amplifying signals representative of evoked responses (e.g., during fitting procedures of cochlear implant system 100 to the patient) and amplifying audio signals received by the microphone (e.g., during normal operation of the cochlear implant system). In other examples, the signal representative of the evoked response and the audio signals received by the microphone may each be amplified by separate, dedicated amplifiers located within sound processor 104.

Additionally, sound processor 104 may process the signal representative of the evoked response by removing at least one stimulus artifact from the signal to generate a processed version of the signal representative of the evoked response, by removing other noise or unwanted artifacts from the signal, by converting the signal from an analog to a digital signal to facilitate further processing or storage of data associated with the signal, by analyzing the timing or other characteristics of particular features (e.g., expected positive vertex waves) of the signal, or by any other means that may serve a particular embodiment. By amplifying the signal detected by conductive contacts 610 and/or 614 prior to otherwise processing the signal, the amplifier may enable sound processor 104 to more effectively and efficiently process the signals in these ways. For example, amplification by an amplifier within sound processor 104 may make the signal large enough to be accurately converted from the analog domain to the digital domain, or may facilitate removal of the stimulus artifact on the signal. However, it will be understood that the signal may be amplified, filtered, and otherwise processed in any order that may serve a particular embodiment.

One advantage of measuring evoked responses using implementation 600 and other implementations of measurement system 500 described herein is that preparing the patient for measuring the evoked responses may be simplified compared to conventional methods, making the measurement process less time-consuming, inconvenient, and/or expensive. For example, rather than using a dedicated ABR machine synchronized with the cochlear implant system (e.g., with sound processor 104) and having a plurality of dedicated electrodes (with accompanying wires connecting each electrode to the ABR machine), conductive contacts may be connected to components of the cochlear implant system that are already in contact with the patient's head at suitable locations for detecting signals representative of evoked responses from the patient's brain.

In certain examples, the conductive contacts may be permanently connected to the components of the cochlear implant system (i.e., in a manner such that they are still connected to the components of the cochlear implant system even when the cochlear implant system operates in a "normal" mode in which the cochlear implant system generates and applies electrical stimulation representative of audio signals to the patient). For example conductive contact 610 may be permanently attached to headpiece 106 and conductive contact 614 may be permanently attached to sound processor 104. As such, conductive wires communicatively coupling the conductive contacts with sound processor 104 may be integrated with cable 606 and/or sound processor 104 such that no additional electrode setup is required to measure evoked responses from the patient's brain. As such, the patient may be able to measure evoked responses more easily outside of a typical clinical setting.

In other examples, the conductive contacts may be temporarily attached to the components of the cochlear implant system (e.g., to headpiece 106 and/or sound processor 104 for use during a fitting procedure) and the conductive wires may be independent from cable 606. However, even this type of implementation may provide significant convenience and/or comfort benefits over conventional setups since the conductive contacts detecting the signals representative of the evoked responses may be configured to easily attach to components already in contact with external surface 602 of the patient's head. In any case, headpiece 106 and sound processor 104 may be the same headpiece and sound processor that the patient uses in the operation of his or her cochlear implant system day to day. For example, in addition to facilitating the measurement of evoked responses from the patient during a fitting procedure, sound processor 104 may be further configured to detect an audio signal presented to the patient subsequent to the detection of the signal representative of the evoked response by conductive contacts 610 and 614 (e.g., subsequent to the fitting procedure), and to transmit, via wireless communication facilitated by headpiece 106 and in response to the detection of the audio signal, a stimulation parameter to a cochlear implant (e.g., cochlear implant 108 in FIG. 1), the stimulation parameter configured to direct the cochlear implant to apply electrical stimulation representative of the audio signal to the patient.

FIG. 7 illustrates another exemplary implementation 700 of measurement system 500. Like implementation 600, in operation, implementation 700 may be attached to, worn by, or otherwise associated with the patient such as by attaching to external surface 602 of the head of the patient, worn behind ear 604 of the patient, etc. Also like implementation 600, implementation 700 may include sound processor 104 communicatively coupled with headpiece 106 by way of cable 606. Implementation 700 may also include conductive contacts 610 and/or 614 located, respectively, between headpiece 106 and external surface 602 and/or between sound processor 104 and external surface 602 as shown in FIG. 6 (not explicitly shown in FIG. 7). Implementation 700 may also be similar to implementation 600 in other respects described above in relation to FIG. 6.

However, unlike implementation 600, implementation 700 shows that sound processor 104 may be communicatively coupled to a programming system such as programming system 302, described above in relation to FIG. 3. For example, as described above in relation to FIG. 4, programming system 302 may be implemented by computing device 402 and CPI device 404. As shown in FIG. 7, sound processor 104 may connect via cable 408 to CPI device 404, which may connect via cable 406 to computing device 402.

Whereas, in implementation 600, sound processor 104 may independently direct the cochlear implant to generate and apply electrical stimulation to the patient and may independently receive and process the signal representative of the evoked response, in implementation 700, programming system 302 (e.g., computing device 402 and/or CPI device 404) may facilitate sound processor 104 in performing one or more of these operations. Specifically, programming system 302 may be separate from and communicatively coupled with sound processor 104, and may be configured to transmit, to sound processor 104, a command for sound processor 104 to direct the cochlear implant (e.g., cochlear implant 108 of FIGS. 1 and 3, not shown in FIG. 7) to generate the electrical stimulation. Programming system 302 may also be configured to receive, from sound processor 104, the signal representative of the evoked response that was received by sound processor 104 from conductive contacts 610 and 614. Finally, programming system 302 may be further configured to process the signal representative of the evoked response by removing at least one stimulus artifact from the signal representative of the evoked response.

It will be recognized that sound processor 104 and programming system 302 may perform the operations described above, as well as any other operations that may facilitate measuring an evoked response, in any combination that may serve a particular embodiment. For example, sound processor 104 may perform these operations independently (e.g., as described in relation to implementation 600 in FIG. 6), programming system 302 may perform one or more of the operations independently (e.g., as described in relation to implementation 700), or programming system 302 and sound processor 104 may cooperate in any suitable way not specifically described herein. While FIGS. 8 and 9, like FIG. 6, do not explicitly illustrate programming system 302, it will be understood that the embodiments described in relation to FIGS. 8, and 9 may each include a programming system that may cooperate with sound processor 104 in any way that may serve a particular implementation.

Figure 8:
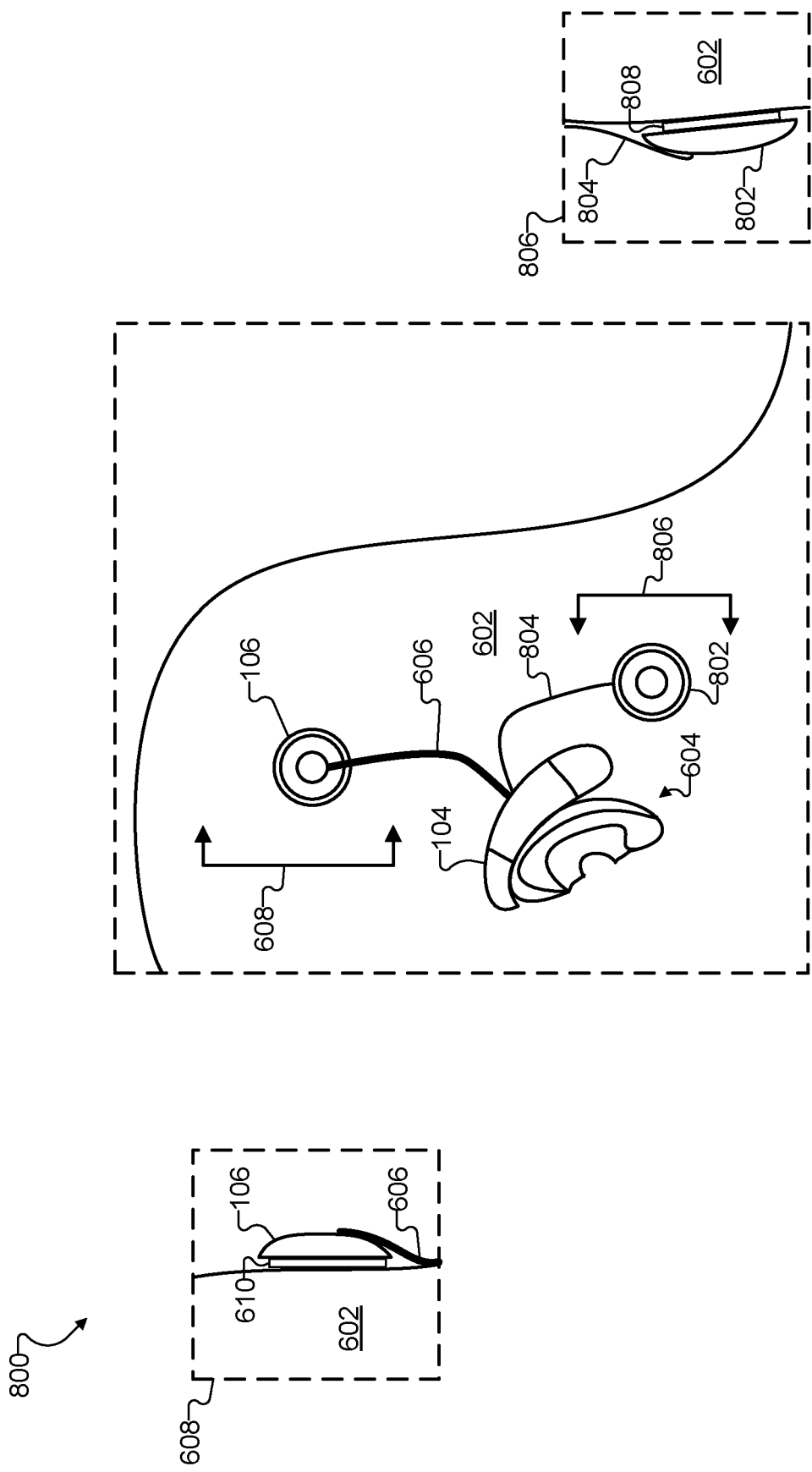

FIG. 8 illustrates another exemplary implementation 800 of measurement system 500. Like implementations 600 and 700, implementation 800 may, in operation, be attached to, worn by, or otherwise associated with the patient such as by attaching to external surface 602 of the head of the patient, worn behind ear 604 of the patient, etc. For example, while sound processor 104 is illustrated as a BTE sound processor in FIG. 8 for simplicity, sound processor 104 may be a body worn device in implementation 800, worn or carried in another suitable location on the patient's body or clothing rather than worn behind ear 604.

As with the implementations described above, sound processor 104 may be communicatively coupled with headpiece 106 by way of cable 606, and conductive contact 610 (e.g., constructed of a conductive cloth such as silver cloth or other suitable material) may be located between headpiece 106 and external surface 602 as shown in view 608. Again, cable 606 may include one or more conductors (e.g., conductive wires) configured to carry electrical signals between headpiece 106 and sound processor 104, such as data signals representative of commands carried from sound processor 104 to be transmitted by headpiece 106 to a cochlear implant implanted within the patient, and electrical signals representative of evoked responses detected by conductive contact 610 carried from conductive contact 610 to sound processor 104.

However, in addition or as an alternative to conductive contact 614 physically coupled to sound processor 104 in implementation 600 (see view 612 in FIG. 6), implementation 800 may include a second headpiece 802 connected via a second cable 804 to sound processor 104. As illustrated, a view 806 shows a right-side view of headpiece 802 and cable 804 where a conductive contact 808 is shown to be physically coupled to headpiece 802 (e.g., under headpiece 802) and located between headpiece 802 and external surface 602 of the head of the patient. Like conductive contact 610, conductive contact 808 may be constructed of any suitable conductive material that is configured to detect signals representative of evoked responses from the brain of the patient by being in contact with external surface 602 of the head of the patient. For example, conductive contact 808 may be constructed of a conductive cloth such as a silver cloth, or another conductive material that may serve a particular embodiment.

Headpiece 802 may be separate from sound processor 104 and may connect to sound processor 104 by way of second cable 804. Headpiece 802 may affix to external surface 602 of the head of the patient in a location on the external surface of the head of the patient apart from where headpiece 106 is affixed. For example, as illustrated in FIG. 8, while headpiece 106 may be located above the ear, nearer the top of the head of the patient, headpiece 802 may be located in an area lower on the head, apart from the location of headpiece 106. For example, the location of headpiece 802 may correspond to a mastoid process of the patient (e.g., located over or near the patient's mastoid process) or may be located near ear 604 in a similar location as to the location of conductive contact 614 in FIG. 6. Conductive contact 808 may be physically coupled to headpiece 802 and configured to be located between headpiece 802 and external surface 602 of the head of the patient while headpiece 802 is affixed to external surface 602 of the head of the patient (e.g., in the location corresponding to the mastoid process of the patient).

While headpiece 106 and sound processor 104 may be the same headpiece and sound processor that the patient uses in the operation of his or her cochlear implant system day to day as explained above, in certain examples, headpiece 802 may be a "dummy" headpiece that may only be used for measuring evoked responses (e.g., in the context of a fitting procedure). For example, headpiece 802 may connect to sound processor 104 by way of cable 804 and may affix to external surface 602 of the head of the patient similarly to headpiece 106, but headpiece 802 may not facilitate wireless communication between sound processor 104 and any cochlear implant implanted within the patient. As such, cable 804 is depicted to be thinner than cable 606 to illustrate that, while cable 606 may include conductive wires for carrying both signals representative of evoked responses and signals representing commands from sound processor 104 to be transmitted by headpiece 106 to a cochlear implant implanted within the patient, cable 804 may only be used for carrying signals representative of evoked responses since headpiece 802 may not be configured to transit commands from sound processor 104 to a cochlear implant implanted within the patient.

Sound processor 104 may include an amplifier (e.g., an amplifier located within sound processor 104) for amplifying the signal representative of the evoked response detected by conductive contacts 610 and/or 808. For example, the signal representative of the evoked response may be amplified to facilitate other processing of the signal as described above (e.g., removing stimulus artifacts or other noise from the signal, converting the signal from an analog to a digital signal, analyzing the timing or other characteristics of the signal, etc.). By amplifying the signal detected by conductive contacts 610 and/or 808 prior to otherwise processing the signal, the amplifier may enable sound processor 104 to more effectively and efficiently process the signals in these ways. The amplifier may be communicatively coupled with each of conductive contacts 610 and 808 (e.g., by cables 606 and 804, respectively), and may be configured to amplify the signal representative of the evoked response to generate an amplified version of the signal representative of the evoked response.

In certain examples, the amplifier may be a shared amplifier configured to operate in a plurality of modes. For example, in a first mode of operation, the shared amplifier may be configured to amplify the signal representative of the evoked response to generate the amplified version of the signal, while in a second mode of operation, the shared amplifier may be configured to amplify an audio signal received by a microphone communicatively coupled with the sound processor (e.g., microphone 102, described above in relation to FIG. 1 but not explicitly shown in FIG. 8). As described above, the shared amplifier may operate in the one or more modes of operation simultaneously or consecutively by, for example, multiplexing the signal representative of the evoked response and the audio signal received by the microphone into the inputs of the shared amplifier. Alternatively, separate, dedicated amplifiers located within sound processor 104 may be employed for amplifying each signal.

While the amplifiers described above (e.g., shared amplifiers, dedicated amplifiers) have been described as being located within sound processor 104, it will be recognized that, in certain implementations, measurement system 500 may include an amplifier located external to sound processor 104, rather than within sound processor 104. As with other amplifiers described above, the external amplifier may be communicatively coupled with sound processor 104 and with each of the conductive contacts in the plurality of conductive contacts. Additionally, the external amplifier may be configured to amplify the signal representative of the evoked response to generate an amplified version of the signal representative of the evoked response that the external amplifier may communicate to sound processor 104.

Figure 9:
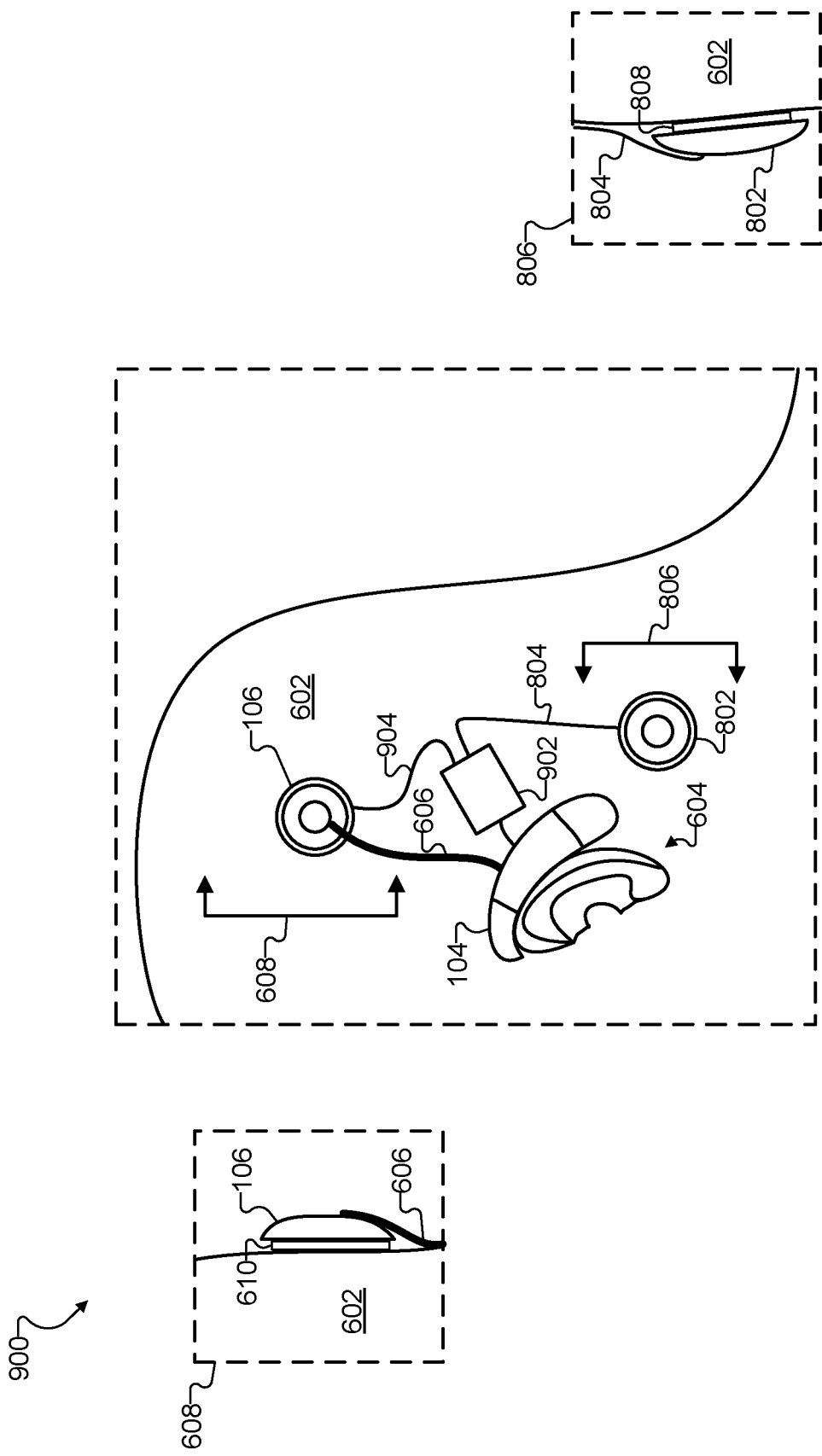

To illustrate, FIG. 9 illustrates another exemplary implementation 900 of measurement system 500. Like implementations 600, 700, and 800 described above, implementation 900 may, in operation, be attached to, worn by, or otherwise associated with the patient such as by attaching to external surface 602 of the head of the patient, to ear 604 of the patient, etc. For example, while sound processor 104 is illustrated as a BTE sound processor in FIG. 9 for simplicity, sound processor 104 may be a body worn device in implementation 900, worn or carried in another suitable location on the patient's body or clothing rather than worn behind ear 604.

Implementation 900 may be similar to implementations 600, 700, and 800 in other ways as well. However, as illustrated in FIG. 9, implementation 900 may include an external amplifier 902, rather than using an amplifier located within sound processor 104. While using an internal amplifier such as those described in relation to FIGS. 6-8 may provide particular benefits related to convenience of setup, using an external amplifier as shown in FIG. 9 may provide benefits related to backwards compatibility and more universal functionality of measurement system 500. Specifically, in implementations where it is difficult or inconvenient to provide the patient with a sound processor or a headpiece configured to implement measurement system 500 (e.g., a sound processor with a shared amplifier and signal multiplexing built in and/or a headpiece associated with a conductive contact configured to detect and communicate signals representative of evoked responses to the sound processor), an external amplifier 902, as well as cables 804 and 904 dedicated to carrying only signals representative of evoked responses, may be employed.

Thus, of the components illustrated in FIG. 9, the patient may ordinarily wear only sound processor 104 and headpiece 106 connected via cable 606. However, when evoked responses are to be measured (e.g., during a fitting procedure in a clinical setting), a clinician measuring the evoked responses may provide headpiece 802, conductive contacts 610 and 808, cables 904 and 804, and external amplifier 902. Measurement system 500 may be implemented by properly connecting the components provided by the clinician with the components worn by the patient as part of the patient's cochlear implant system, as illustrated.

The examples and explanation above have illustrated various methods and systems whereby evoked responses may be measured from a patient's brain by causing electrical stimulation to be generated and applied to the patient, and then by detecting evoked responses of the brain to the electrical stimulation (e.g., using conductive contacts attached to one or more headpieces or a sound processor of a cochlear implant system). As mentioned above, unlike certain conventional measurement systems (e.g., ABR machines), which may be limited to measuring only a particular type of evoked response, methods and systems described herein may be operative to measure various types of evoked responses (e.g., evoked responses measured with differing latencies from the onset of the electrical stimulation being applied to the patient) that may be generated by various types of electrical stimulation (e.g., electrical stimulation that lasts for varying amounts of time).

To illustrate, FIG. 10 (e.g., FIGS. 10A and 10B) illustrates exemplary timing diagrams of evoked responses to different types of electrical stimulation. In particular, FIG. 10 illustrates an exemplary EABR 1002 occurring on a time scale of approximately ten milliseconds with an exemplary stimulus 1004 configured to evoke EABR 1002 (FIG. 10A), as well as an exemplary central auditory response 1006 occurring on a time scale of several hundred milliseconds with an exemplary stimulus 1008 configured to evoke central auditory response 1006 (FIG. 10B). As shown, both stimuli (e.g., stimuli 1004 and 1008) are illustrated on respective timelines 1010 (e.g., timeline 1010-A in FIG. 10A and timeline 1010-B in FIG. 10B) along with the respective evoked responses (e.g., EABR 1002 and central auditory response 1006) that the stimuli are configured to evoke.

In the example of FIG. 10A, the electrical stimulation represented by stimulus 1004 may be a single pulse. As shown in FIG. 10A, stimulus 1004 may only last for approximately 100 microseconds (i.e., 0.1 milliseconds), and may evoke in a cochlear implant patient a similar response that an auditory "click" sound would evoke in a patient with typical hearing capability. In response to the single pulse of stimulus 1004, an evoked response in the form of EABR 1002 may be generated by the brain of the patient during a time period beginning approximately one millisecond after onset of stimulus 1004 to the patient by the cochlear implant and ending approximately ten milliseconds after the onset of stimulus 1004. In certain examples, EABR 1002 may include a series of vertex positive waves such as waves commonly referred to in the art as wave I (occurring between approximately one and two milliseconds after onset of stimulus 1004), wave II (occurring between approximately two and three milliseconds after onset of stimulus 1004), wave III (occurring between approximately three and four milliseconds after onset of stimulus 1004), wave IV (occurring between approximately four and five milliseconds after onset of stimulus 1004), wave V (occurring between approximately five and six milliseconds after onset of stimulus 1004), wave VI (occurring between approximately six and seven milliseconds after onset of stimulus 1004), and wave VII (occurring between approximately eight and nine milliseconds after onset of stimulus 1004), one or more of which may be analyzed by a clinician measuring the EABR as part of a fitting procedure.

In the example of FIG. 10B, the electrical stimulation represented by stimulus 1008 may be a pulse train including a series of consecutive pulses similar to the single pulse described above in relation to stimulus 1004. As shown in FIG. 10B, stimulus 1008 may last significantly longer than stimulus 1004. For example, stimulus 1008 may last for approximately one hundred milliseconds, and may evoke in a cochlear implant patient a similar response that a series of auditory "click" sounds would evoke in a patient with typical hearing capability. In response to the pulse train of stimulus 1008, an evoked response in the form of central auditory response 1006 may be generated by the brain of the patient during a time period beginning approximately fifty milliseconds after onset of stimulus 1008 to the patient by the cochlear implant and ending approximately three hundred milliseconds after the onset of stimulus 1008. In certain examples, central auditory response 1006 may include a series of vertex positive waves such as waves commonly referred to in the art as wave P1 (occurring around approximately fifty milliseconds after onset of stimulus 1008) wave P2 (occurring between approximately one hundred and two hundred milliseconds after onset of stimulus 1008), and/or other waves known in the art, one or more of which may be analyzed by a clinician measuring the central auditory response as part of a fitting procedure.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a compact disc read-only memory ("CD-ROM"), a digital video disc ("DVD"), any other optical medium, random access memory ("RAM"), programmable read-only memory ("PROM"), erasable programmable read-only memory ("EPROM"), electrically erasable programmable read-only memory ("EEPROM"), a Flash EEPROM device, any other memory chip or cartridge, or any other tangible medium from which a computer can read.

Figure 11:
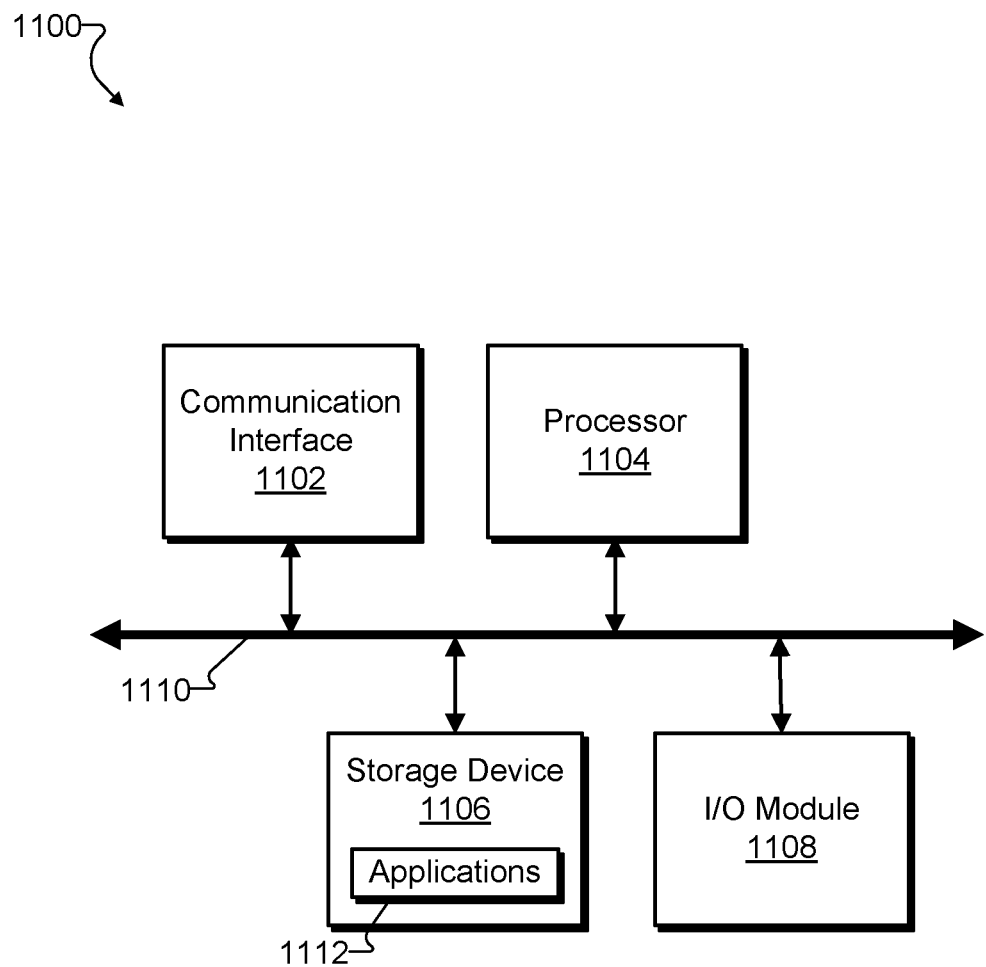
FIG. 11 illustrates an exemplary computing device according to principles described herein.

FIG. 11 illustrates an exemplary computing device 1100 that may be specifically configured to perform one or more of the processes described herein. As shown in FIG. 11, computing device 1100 may include a communication interface 1102, a processor 1104, a storage device 1106, and an input/output ("I/O") module 1108 communicatively connected via a communication infrastructure 1110. While an exemplary computing device 1100 is shown in FIG. 11, the components illustrated in FIG. 11 are not intended to be limiting. Additional or alternative components may be used in other embodiments. Components of computing device 1100 shown in FIG. 11 will now be described in additional detail.

Communication interface 1102 may be configured to communicate with one or more computing devices. Examples of communication interface 1102 include, without limitation, a wired network interface (such as a network interface card), a wireless network interface (such as a wireless network interface card), a modem, an audio/video connection, and any other suitable interface.

Processor 1104 generally represents any type or form of processing unit capable of processing data or interpreting, executing, and/or directing execution of one or more of the instructions, processes, and/or operations described herein. Processor 1104 may direct execution of operations in accordance with one or more applications 1112 or other computer-executable instructions such as may be stored in storage device 1106 or another computer-readable medium.

Storage device 1106 may include one or more data storage media, devices, or configurations and may employ any type, form, and combination of data storage media and/or device. For example, storage device 1106 may include, but is not limited to, a hard drive, network drive, flash drive, magnetic disc, optical disc, RAM, dynamic RAM, other non-volatile and/or volatile data storage units, or a combination or sub-combination thereof. Electronic data, including data described herein, may be temporarily and/or permanently stored in storage device 1106. For example, data representative of one or more executable applications 1112 configured to direct processor 1104 to perform any of the operations described herein may be stored within storage device 1106. In some examples, data may be arranged in one or more databases residing within storage device 1106.

I/O module 1108 may be configured to receive user input and provide user output and may include any hardware, firmware, software, or combination thereof supportive of input and output capabilities. For example, I/O module 1108 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1108 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1108 is configured to provide graphical data to a display for presentation to a user. The graphical data may be representative of one or more graphical user interfaces and/or any other graphical content as may serve a particular implementation.

In some examples, any of the facilities or systems described herein may be implemented by or within one or more components of computing device 1100. For example, one or more applications 1112 residing within storage device 1106 may be configured to direct processor 1104 to perform one or more processes or functions associated with detecting facility 502 and/or recording facility 504. Likewise, storage facility 506 may be implemented by or within storage device 1506.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
   a sound processor configured to be worn by a patient and to direct a cochlear implant implanted within the patient to apply electrical stimulation to the patient; and
   a conductive contact configured to detect a signal representative of an evoked response generated by a brain of the patient, the conductive contact integrated with the sound processor so as to be located between the sound processor and an external surface of a head of the patient while the sound processor is worn by the patient.

2. The system of claim 1, further comprising:
a headpiece separate from the sound processor and configured to connect to the sound processor by way of a cable and to affix to the external surface of the head of the patient; and
an additional conductive contact configured to detect the signal representative of the evoked response, the additional conductive contact integrated with the headpiece so as to be located between the headpiece and the external surface of the head of the patient while the headpiece is affixed to the external surface of the head of the patient.

3. The system of claim 2, wherein the headpiece is an operational headpiece that is further configured to facilitate wireless communication between the sound processor and the cochlear implant by transmitting, when affixed to the external surface of the head of the patient, a wireless signal from the sound processor to the cochlear implant implanted within the patient.

4. The system of claim 2, wherein the headpiece is a dummy headpiece that is configured for use in detecting the evoked response but is not further configured to facilitate wireless communication between the sound processor and the cochlear implant.

5. The system of claim 1, wherein the sound processor is configured to direct the cochlear implant to apply the electrical stimulation to the patient by:
detecting an audio signal presented to the patient subsequent to detection, by the conductive contact, of the signal representative of the evoked response generated by the brain of the patient; and
transmitting, in response to the detecting of the audio signal, a stimulation parameter to the cochlear implant, the stimulation parameter configured to direct the cochlear implant to apply electrical stimulation representative of the audio signal to the patient.

6. The system of claim 1, further comprising an amplifier located within the sound processor, the amplifier communicatively coupled with the conductive contact and configured to amplify the signal representative of the evoked response to generate an amplified version of the signal representative of the evoked response.

7. The system of claim 6, wherein the amplifier is a shared amplifier configured:
in a first mode of operation, to amplify the signal representative of the evoked response to generate the amplified version of the signal; and
in a second mode of operation, to amplify an audio signal received by the sound processor.

8. The system of claim 1, wherein:
the electrical stimulation applied to the patient is configured to evoke the evoked response generated by the brain of the patient; and
the conductive contact detects the signal representative of the evoked response generated by the brain of the patient in response to the electrical stimulation being applied to the patient.

9. The system of claim 1, wherein:
the electrical stimulation applied to the patient is a single pulse;
the evoked response is generated by the brain of the patient in response to the single pulse during a time period beginning 1 millisecond (ms) after onset of the electrical stimulation applied to the patient by the cochlear implant and ending 10 ms after the onset of the electrical stimulation; and
the evoked response is an electroauditory brainstem response.

10. The system of claim 1, wherein:
the electrical stimulation applied to the patient is a pulse train including a series of consecutive pulses;
the evoked response is generated by the brain of the patient in response to the pulse train during a time period beginning 50 milliseconds (ms) after onset of the electrical stimulation applied to the patient by the cochlear implant and ending 300 ms after the onset of the electrical stimulation; and
the evoked response is a central auditory response.

11. The system of claim 1, wherein the sound processor is further configured to:
receive, from the conductive contact, the signal representative of the evoked response; and
process the signal representative of the evoked response by removing at least one stimulus artifact from the signal representative of the evoked response.

12. The system of claim 1, further comprising a programming system separate from and communicatively coupled with the sound processor, the programming system configured to:
transmit, to the sound processor, a command for the sound processor to direct the cochlear implant to generate the electrical stimulation;
receive, from the sound processor, the signal representative of the evoked response after the signal is received by the sound processor from the conductive contact; and
process the signal representative of the evoked response by removing at least one stimulus artifact from the signal representative of the evoked response.

13. The system of claim 1, wherein the sound processor is implemented by a behind-the-ear (BTE) device configured to be worn by the patient behind an ear of the patient.

14. A system comprising:
a sound processor configured to be worn by a patient and to direct a cochlear implant implanted within the patient to apply electrical stimulation to the patient;
a headpiece separate from the sound processor and including a first coil configured to transmit, when affixed to an external surface of a head of the patient, a wireless signal from the sound processor to a second coil implanted within the patient and associated with the cochlear implant; and
a plurality of conductive contacts configured, when affixed to an external surface of the head of the patient, to detect a signal representative of an evoked response generated by a brain of the patient, the plurality of conductive contacts including:
a first conductive contact integrated with the sound processor so as to be located between the sound processor and the external surface of the head of the patient while the sound processor is worn by the patient, and
a second conductive contact integrated with the headpiece so as to be located between the headpiece and the external surface of the head of the patient while the headpiece is affixed to the external surface of the head of the patient.

15. The system of claim 14, further comprising an amplifier located within the sound processor, the amplifier communicatively coupled with the plurality of conductive contacts and configured to amplify the signal representative of the evoked response to generate an amplified version of the signal representative of the evoked response.

16. The system of claim 14, wherein:
the electrical stimulation applied to the patient is a single pulse;
the evoked response is generated by the brain of the patient in response to the single pulse during a time period beginning 1 millisecond (ms) after onset of the electrical stimulation applied to the patient by the cochlear implant and ending 10 ms after the onset of the electrical stimulation; and
the evoked response is an electroauditory brainstem response.

17. The system of claim 14, wherein:
the electrical stimulation applied to the patient is a pulse train including a series of consecutive pulses;
the evoked response is generated by the brain of the patient in response to the pulse train during a time period beginning 50 milliseconds (ms) after onset of the electrical stimulation applied to the patient by the cochlear implant and ending 300 ms after the onset of the electrical stimulation; and
the evoked response is a central auditory response.

18. The system of claim 14, wherein the sound processor is further configured to:
receive, from the plurality of conductive contacts, the signal representative of the evoked response; and
process the signal representative of the evoked response by removing at least one stimulus artifact from the signal representative of the evoked response.

19. The system of claim 14, further comprising a programming system separate from and communicatively coupled with the sound processor, the programming system configured to:
transmit, to the sound processor, a command for the sound processor to direct the cochlear implant to generate the electrical stimulation;
receive, from the sound processor, the signal representative of the evoked response after the signal is received by the sound processor from the plurality of conductive contacts; and
process the signal representative of the evoked response by removing at least one stimulus artifact from the signal representative of the evoked response.

20. A method comprising:
directing, by a sound processor configured to be worn by a patient, a cochlear implant implanted within a head of the patient to apply electrical stimulation to the patient; and
detecting, by the sound processor via a conductive contact integrated with the sound processor so as to be located between the sound processor and an external surface of the head of the patient while the sound processor is worn by the patient, a signal representative of an evoked response generated by a brain of the patient.

* * * * *